(12) United States Patent
Graziani et al.

(10) Patent No.: US 11,653,961 B2
(45) Date of Patent: May 23, 2023

(54) TRANSPEDICULAR ANCHORING SCREW WITH REINFORCED SECONDARY STABILITY

(71) Applicant: SPINEDUST, Marseilles (FR)

(72) Inventors: Noël Graziani, Marseilles (FR); Olivier Levrier, Marseilles (FR)

(73) Assignee: SPINEDUST, Marseilles (FR)

( * ) Notice: Subject to any disclaimer, the term of this patent is extended or adjusted under 35 U.S.C. 154(b) by 0 days.

(21) Appl. No.: 17/775,426

(22) PCT Filed: Nov. 5, 2020

(86) PCT No.: PCT/HR2020/052000
§ 371 (c)(1),
(2) Date: May 9, 2022

(87) PCT Pub. No.: WO2021/089944
PCT Pub. Date: May 14, 2021

(65) Prior Publication Data
US 2022/0378487 A1    Dec. 1, 2022

(30) Foreign Application Priority Data
Nov. 7, 2019 (FR) ...................... 1912517

(51) Int. Cl.
*A61B 17/86* (2006.01)
*A61B 17/70* (2006.01)
*A61B 17/00* (2006.01)

(52) U.S. Cl.
CPC ........ *A61B 17/863* (2013.01); *A61B 17/7001* (2013.01); *A61B 17/866* (2013.01);
(Continued)

(58) Field of Classification Search
CPC .................................................. A61B 17/863
See application file for complete search history.

(56) References Cited

U.S. PATENT DOCUMENTS

2007/0043372 A1* 2/2007 Willmann ............ A61B 17/863
606/264

FOREIGN PATENT DOCUMENTS

| EP | 1682021 A1 | 7/2006 |
| EP | 3329871 A1 | 6/2018 |
| WO | 2014184463 A1 | 11/2014 |

OTHER PUBLICATIONS

International Search Report dated Mar. 3, 2021 re: Application No. PCT/FR2020/052000, pp. 1-2, citing: EP 3329871 A1.
(Continued)

*Primary Examiner* — Olivia C Chang
(74) *Attorney, Agent, or Firm* — Cantor Colburn LLP

(57) ABSTRACT

A transpedicular anchoring screw including a screw body having a first helical thread having:includes
  a proximal portion, having notched portions inscribed within notched angular sectors and separated by separation portions inscribed within separation angular sectors, where, over a screw pitch, a ratio between the sum of the measurements of the separation angular sectors and the sum of the measurements of the notched angular sectors is between 50% and 150%.

The anchoring screw also includes a distal portion, having notched portions inscribed within notched angular sectors and separated by separation distal portions inscribed within separation angular sectors, where, over a screw pitch, a ratio between the sum of the measurements of the separation angular sectors and the sum of the measurements of the notched angular sectors is between 0% and 10%.

17 Claims, 7 Drawing Sheets

(52) U.S. Cl.
CPC ............... *A61B 2017/00004* (2013.01); *A61B 2017/8655* (2013.01)

(56) References Cited

OTHER PUBLICATIONS

Written Opinion dated Mar. 3, 2021 re: Application No. PCT/FR2020/052000, pp. 1-11, citing: EP 3329871 A1.

* cited by examiner

TRANSPEDICULAR ANCHORING SCREW WITH REINFORCED SECONDARY STABILITY

TECHNICAL FIELD

The present disclosure concerns a transpedicular anchoring screw, suitable for anchorage in the pedicle of a vertebra of a human body.

BACKGROUND

In the surgical field, it is known to use spinal implants fastened on one or several vertebra(e) by means of one or several anchoring screw(s). For example, it is known to fasten vertebral arthrodesis implants on two successive vertebrae enabling a fusion of these two vertebrae and a general stabilization of the spine.

In general, such implants are fastened on the vertebrae by means of anchoring screws specially adapted to cooperate with said implants and penetrating into the bone structure of the vertebrae.

Thus, each anchoring screw allows ensuring a reliable anchorage of an implant on a vertebra characterized by:
  a primary stability, resulting from the mechanical forces exerted between the bone of the vertebra and the anchoring screw as soon as the latter is inserted into the vertebra, and
  a secondary stability, resulting from an osseointegration process, that is to say resulting from bone regeneration and bone remodeling occurring around the anchoring screw after insertion thereof into the vertebra.

Thus, the quality of the primary stability and of the secondary quality conferred by an anchoring screw depends on several different parameters, and in particular on the geometry of the anchoring screw, the quality of the bone structure of the vertebra in which it is inserted, or else of the position of insertion of the anchoring screw with respect to the vertebra.

More specifically, an anchoring screw could be inserted into a vertebra via an anterior approach, the anchoring screw then passing only through the vertebral body of said vertebra, or via a posterior approach, the anchoring screw then passing first through a pedicle then through the vertebral body of said vertebra.

In the case of a posterior approach, the anchoring screw, once implanted, passes through three types of bone structures of the vertebra, each presenting different mechanical properties:
  the cortical wall of the pedicle, formed of a compact and hard bone,
  a central portion of the pedicle, formed of a quite dense spongy bone, and
  a spongy body of the vertebral body, formed of a less dense and more fragile bone.

It should also be noted that it could be considered that the anchoring screw is able to pass, at the end of its rod, through the cortical wall of the vertebral body, formed of a compact and hard bone.

Hence, each of these bone structures participates in the primary stability of the anchoring screw in an unequal way, the cortical walls of the pedicle and the vertebral body offering a strong and solid anchorage whereas the spongy body of the vertebral body confers a much lower, and even non-existing, primary stability.

Thus, it is usual to adapt the geometry of the anchoring screw to improve the primary stability of the latter, by increasing the size of the contact surfaces between the latter and the cortical walls of the pedicle and of the vertebral body.

It is also already known from the prior art to modify the structure of the anchoring screw in order to improve its secondary stability.

For example, each of the documents WO 14184463 and EP1682021 describe an anchoring screw having a helical thread including several lateral notches with the same size and shape: once such a screw is implanted in a vertebra, the bone proximate to the anchoring screw is brought to regenerate and bone growth takes place into the notches, filling them and thus increasing the contact surface with the anchoring screw.

However, due to the small size of these notches, these allow improving the secondary stability of the anchoring screw only marginally.

In addition, such anchoring screws having a single type of notches face an incompatibility:
  in the case where the notches are small-sized, they do not fully profit from the secondary stability potentially conferred by the spongy body of the vertebral body, and
  in the case where the notches are large-sized, they degrade the primary stability of the anchoring screw, due to the reduction in the size of the contact surfaces between the latter and the cortical walls of the pedicle.

In turn, the document EP3329871 describes an anchoring screw whose thread includes a first distal portion (proximate to the tip of the anchoring screw) and a proximal portion (proximate to the head of the anchoring screw) of different structure, the thread having in the distal portion serrations that are absent from the proximal portion.

However, this anchor screw has two major drawbacks:
  due to the absence of serrations in the proximal portion, this anchoring screw does not profit from the secondary stability potentially conferred by the cortical wall and the central portion of the pedicle; and
  due to the immediate proximity between the tip of the anchoring screw and the serrate thread, it could damage the neighboring bone structures during the implantation thereof, thus deteriorating its primary stability and increasing the vascular and neurological risks incurred by a patient, in particular an osteopenic patient.

SUMMARY

Thus, the present disclosure aims at solving all or part of the aforementioned drawbacks, by providing a transpedicular anchoring screw having a reinforced secondary stability, without degrading its primary stability.

Another objective of the disclosure is to provide a transpedicular anchoring screw whose implantation in a vertebra is not deleterious, that is to say is not likely to damage the bone structure of said vertebra.

Still another aim of the disclosure is to provide a transpedicular anchoring screw which can be implanted in a vertebra using standard tools and which remains simple to use and inexpensive to manufacture.

To this end, it provides a transpedicular anchoring screw, adapted for anchorage in a pedicle of a vertebra, including a screw body extending along a screw axis between a proximal end and a distal end, said screw body having a first thread and a second thread, each of said first thread and second thread being helical-shaped with the same screw pitch, extending between said proximal end and said distal end and having a convex-shaped outer edge, said transpedicular anchoring screw being remarkable in that at least said first thread has, from the proximal end towards the distal end, at least:

a proximal portion, in which the outer edge of said first thread has a series of notched proximal portions, each defined by a proximal notch formed in said outer edge and inscribed within a notched proximal angular sector, wherein two successive notched proximal portions are separated from each other by a separation proximal portion, in which said outer edge is not notched and is inscribed within a separation proximal angular sector, and wherein, over a length of the first thread corresponding to one screw pitch, a ratio between the sum of the measurements of all of the separation proximal angular sectors and the sum of the measurements of all of the notched proximal angular sectors is comprised between 50% and 150%; and a distal portion, in which the outer edge of said first thread has a series of notched distal portions, each defined by a distal notch formed in said outer edge and inscribed within a notched distal angular sector, wherein two successive notched distal portions are separated by a separation distal portion, in which said outer edge is not notched and is inscribed within a separation distal angular sector, and wherein, over a length of the first thread corresponding to one screw pitch, a ratio between the sum of the measurements of all of the separation distal angular sectors and the sum of the measurements of all of the notched distal angular sectors is comprised between 0% and 10%.

Thus, the disclosure provides a transpedicular anchoring screw with a double helical thread, the geometry of one of its two threads being specially adapted to improve the secondary stability of the transpedicular anchoring screw according to the disclosure, without degrading its primary stability.

Indeed, a first thread of the transpedicular anchoring screw according to the disclosure has a generally convex outer edge, for example a circular helical shape, in which notches with variable size and shape are formed.

These notches, once the transpedicular anchoring screw has been implanted in a vertebra, promote bone regeneration of said vertebra and are intended to be at least partially filled with bone structures upon completion of a certain time interval, thus improving the secondary stability of the transpedicular anchoring screw thanks to the increase in the size of the contact surfaces between said transpedicular anchoring screw and said vertebra.

More particularly, the first thread of the transpedicular anchoring screw has two distinct geometry portions:

a proximal portion, intended to be implanted in a pedicle of a vertebra, in which the first thread has a series of proximal notches (defining notched portions proximal to the outer edge of said first thread) separated from each other by separation proximal portions, said separation proximal portions being non-notched and having a large width, measured along the outer edge; and a distal portion, intended to be implanted in the spongy body of the vertebral body of the same vertebra, in which the first thread has a series of distal notches (defining notched portions distal to the outer edge of said first thread) separated from each other others by separation distal portions, said separation distal portions being non-notched and having a width, measured along the outer edge, that is small or even zero. Hence, the first thread has, in its distal portion, a series of distal notches, with a generally concave shape and very close to each other: this first thread therefore has a "star"-like shape, the separation distal portions (disposed between the distal notches) constituting sharp point-shaped radial projections.

This particular structure of the distal thread has two main advantages:

thanks to the large surface occupied by the distal notches, these promote a significant bone regeneration of the vertebra around the distal portion of the first thread, thereby greatly improving the secondary stability of the transpedicular anchoring screw; and during the insertion of the transpedicular anchoring screw into the vertebra, the radial projections formed by the distal notches create at their periphery a bone remodeling area also promoting the secondary stability of the transpedicular anchoring screw.

The proximal notches, formed in the proximal portion of the first thread, are also intended to increase the secondary stability of the transpedicular anchoring screw, by promoting bone regeneration of the pedicle in which this proximal portion is implanted.

However, the surface occupied by these proximal notches is much smaller than that occupied by the distal notches (because of the larger width of the separation proximal portions), in order to preserve the primary stability of the transpedicular anchoring screw.

Indeed, as mentioned before, the primary stability of the transpedicular anchoring screw results primarily from the mechanical forces exerted thereon by the bone structures of the vertebra in which it is implanted, at the level of the cortical wall and the central portion of the pedicle: the primary stability of the transpedicular anchoring screw thus primarily depends on the size of the contact surface between the proximal portion of the first thread and the bone structures of said pedicle.

In order to preserve such a contact surface, it is therefore necessary to restrict the size of the proximal notches and to increase that of the separation proximal portions.

Yet, the spongy body in which the distal portion is intended to be implanted contributes only very slightly to the primary stability of the transpedicular anchoring screw: the increase in the surface occupied by the distal notches and the reduction of that of the separation distal portions decreases the primary stability of the transpedicular anchoring screw only marginally.

Thus, by providing a first thread having proximal and distal notches whose size and/or shape varies according to their area of implantation (spongy body of the vertebral body or denser pedicle bone), the transpedicular according to the disclosure actually has a reinforced secondary stability, without its primary stability being substantially modified.

It should be noted that, in the context of the disclosure, the width of the notched distal portions, of the notched proximal portions, of the separation distal portions and of the separation proximal portions is measured along the outer edge, and is characterized in an equivalent manner by the notched or separation, distal or proximal, angular sectors (observed from the screw axis) in which each of these portions is inscribed.

In particular, each of the notched proximal and distal portions are defined respectively by a proximal or distal notch: their "width" corresponds to the notched proximal or distal angular sector under which said notch is viewed from the screw axis.

In the context of the disclosure, each proximal (respectively distal) notch is thus contiguous to a proximal (respectively distal) separation portion, and vice versa.

In the proximal portion, over a length of the first thread corresponding to one screw pitch (that is to say the interval in which the first thread performs a winding of a complete 360° turn around the screw body), the ratio between the sum of the measurements of all of the separation proximal angular sectors and the sum of the measurements of all of the notched proximal angular sectors is comprised between 50% and 150%: in other words, the notched proximal angular sectors occupy a portion of the first thread substantially equivalent to that occupied by the separation proximal angular sectors (one of these respective portions cannot be more than twice as large as the other).

In this way, the proximal portion confers on the transpedicular anchoring screw good primary stability because the latter remains in contact (through the separation proximal portions) with the cortical bone of the pedicle in which said transpedicular anchoring screw is implanted.

Conversely, in the distal portion, over a length of the first thread corresponding to one screw pitch, the ratio between the sum of the measurements of all of the separation distal angular sectors and the sum of the measurements of all of the notched distal angular sectors is comprised between 0% and 10%: in other words, the notched distal angular sectors occupy a portion of the first thread that is very much larger (at least ten times larger) than that occupied by the separation distal angular sectors.

In this way, the distal portion confers on the transpedicular anchoring screw a very good secondary stability but a lower primary stability.

It should be noted that, in the context of the disclosure, the ratio between the sum of the measurements of all of the separation angular sectors and the sum of the measurements of all of the notched angular sectors corresponds to the result of an operation of dividing the sum of the measurements of all of the separation angular sectors by the sum of the measurements of all of the notched angular sectors.

According to one feature, in the proximal portion, the measurement of each separation proximal angular sector is greater than 15°.

According to another feature, in the distal portion, the measurement of each separation distal angular sector is less than 5°.

The transpedicular anchoring screw according to the disclosure also has a second thread, interlaced with the first thread, having a helical shape and a pitch similar to the latter.

In a first embodiment, the outer edge of this second thread is devoid of distal or proximal notches.

In this way, the transpedicular anchoring screw has, along the screw axis, an alternation between the first thread, including proximal and distal notches, and the second thread, devoid of notches and having a standard profile: the presence of the second thread allows in particular increasing the outer contact surface of the transpedicular anchoring screw proximate to the distal portion of the first thread.

In particular, this alternation of the two threads allows:
  increasing the primary stability of the transpedicular anchoring screw, due to the increase in the size of the contact surface between the latter and the bone structures of a vertebra in which it is implanted, and
  "protecting" said bone structures from possible degradations caused by the radial projections of the distal portion of the first thread during the implantation of the transpedicular anchoring screw.

In one variant, the second thread has, from the proximal end towards the distal end, at least:
  a proximal portion, in which the outer edge of said second thread has a series of notched proximal portions, each defined by a proximal notch formed in said outer edge and inscribed within a notched proximal angular sector, wherein two successive notched proximal portions are separated from each other by a separation proximal portion, in which said outer edge is not notched and is inscribed within a separation proximal angular sector, and wherein, over a length of the second thread corresponding to one screw pitch, a ratio between the sum of the measurements of all of the separation proximal angular sectors and the sum of the measurements of all of the notched proximal angular sectors is comprised between 50% and 150%; and
  a distal portion, in which the outer edge of said second thread has a series of notched distal portions, each defined by a distal notch formed in said outer edge and inscribed within a notched distal angular sector, wherein two successive notched distal portions are separated by a separation distal portion, in which said outer edge is not notched and is inscribed within a separation distal angular sector, and wherein, over a length of the second thread corresponding to one screw pitch, a ratio between the sum of the measurements of all of the separation distal angular sectors and the sum of the measurements of all of the notched distal angular sectors is comprised between 0% and 10%.

In other words, it could be considered that, in a second embodiment of the disclosure, the second thread has the same type of notch and in the same proportion as the first thread. Advantageously, the transpedicular anchoring screw according to the disclosure has a screw head, adapted to cooperate with a surgical implant intended to be fastened on a vertebra, disposed at the proximal end and a leading edge, adapted to promote the penetration of said anchoring screw in said vertebra, disposed at the distal end.

It could be considered that, upon completion of an implantation of the transpedicular anchoring screw according to the disclosure in a vertebra, the leading edge is anchored in the cortical wall of the body of the vertebra, thus improving the primary stability of said transpedicular anchor screw.

It should be noted that, during an implantation of the transpedicular anchoring screw according to the disclosure in a vertebra, the distal portion of the first thread passes through the pedicle of said vertebra, before penetrating into the spongy body of said vertebra body.

In one variant, the distal portion of the first thread extends up to the leading edge. It should be noted that the distal notches may be provided over all or part of the distal portion.

Many embodiments concerning the number, size, shape or distribution of the proximal and distal notches along the first thread could be considered, some of which are described, without limitation, hereinafter.

In one embodiment, each proximal notch has an identical shape and wherein each separation proximal portion is inscribed within a respective separation proximal angular sector with an identical extent, so that said proximal notches are evenly spaced from each other along said first thread.

According to one feature, each notched proximal portion and each separation proximal portion is inscribed within a respective notched proximal angular sector or separation proximal angular sector with an identical measurement within 5°.

Thus, the separation proximal portions and the notched proximal portions have an approximately equal width, and respectively occupy a surface with an equivalent size: the primary stability of the transpedicular anchoring screw according to the disclosure is thus preserved.

According to another possibility, the measurement of each of said notched proximal angular sectors or separation proximal angular sectors is comprised between 30° and 75°.

In an interval corresponding to one pitch of the first thread, said first thread therefore has about three proximal notches and three separation proximal portions, disposed between said proximal notches.

Of course, other embodiments could be considered, wherein each proximal notch has a different shape and/or size and/or width, or wherein the difference in width between the separation proximal portions and the notched proximal portions is more marked.

In one variant, a projection distance of the separation proximal portions is between 1 and 3 times larger than a minimum projection distance of the notched proximal portions.

According to one feature, at least one of the proximal notches is delimited by a single notch edge shaped as a concave circle arc.

For example, the outer edge may thus be in the form of an alternation of sections of convex circle arcs (corresponding to the separation proximal portions) and of concave circle arcs (corresponding to the notched proximal portions).

It should be noted that, in the context of the disclosure, each of the proximal or distal notches has a concave general shape, since it is defined as a recess in the first thread.

According to another feature, at least one of the proximal notches is delimited by a notch edge shaped as a convex circle arc.

For example, the outer edge may have, at the level of each separation proximal portion, a convex circle arc shape with a given radius, and each proximal notch may have a notch edge shaped as a convex circle arc with a radius smaller than said radius, said notch edge joining said outer edge via two side flanges extending radially with respect to the screw axis.

Advantageously, the proximal portion and the distal portion are contiguous, one of the separation proximal portions of the proximal portion being contiguous to one of the notched distal portions of the distal portion.

Thus, the transpedicular anchoring screw according to the disclosure does not have an intermediate portion, in which the first thread would include neither distal notch nor proximal notch: the secondary stability of said transpedicular anchoring screw is therefore improved over the entire measurement of the latter along the screw axis.

In one embodiment, each of the separation distal portions is inscribed within a separation distal angular sector whose measurement is equal to 0°, so that the successive distal notches are contiguous.

In this embodiment, the surface occupied by the separation distal portions is therefore minimum, thereby promoting the secondary stability of the transpedicular anchoring screw and increasing the effect of bone remodeling at the periphery of the distal portion of the first thread, the radial projections formed by the distal notches then being more pointed and sharp.

In one variant, a projection distance of the separation distal portions is comprised between 1 and 3 times larger than a minimum projection distance of the notched distal portions.

According to one feature, at least one of the distal notches is delimited by a single notch edge shaped as a concave circle arc.

In one variant, each distal notch has an identical shape.

For example, the outer edge may be (in the distal portion of the first thread) in the form of an uninterrupted series of sections shaped as a concave circle arc (each of them defining a recessed distal notch), each separation portion being reduced to the point of contact between said sections.

According to another feature, each notched distal portion is inscribed within a notched distal angular sector whose measurement is comprised between 50° and 75°.

In an interval corresponding to the pitch of the first thread, said first thread therefore has about six contiguous proximal notches, defining six radial projections therebetween.

Of course, other embodiments could be considered, wherein each distal notch has a variable shape and/or size and/or width.

According to one possibility, the notched proximal portions and the separation proximal portions of the proximal portion have a thickness, measured along the screw axis, larger than a thickness of the notched distal portions and of the separation distal portions of the distal portion.

According to another possibility, the screw body has a transverse dimension, measured perpendicularly to the screw axis, whose measurement progressively decreases between the proximal end and the distal end.

Hence, the distal portion of the first thread has a thickness and a diameter (measured transversely to the screw axis) smaller than those of the proximal portion: in this way, the distal portion does not damage, during the insertion thereof into the pedicle of a vertebra before reaching the spongy body of the vertebral body of this vertebra, the bone structure of the latter corresponding to the ultimate implantation area of the proximal portion.

Thus, the primary stability of the transpedicular anchoring screw is not degraded by the prior passage of the distal portion of the first thread in the pedicle of a vertebra.

Advantageously, the proximal portion and the distal portion of the first thread extend respectively, along the screw axis, over a proximal length and a distal length, said proximal length having a measurement comprised between 0.5 and 1.5 times that of said distal length.

According to one possibility, the transpedicular anchoring screw includes a screw head positioned on the proximal end of the screw body, said screw head having a collar delimited by a convex-shaped collar edge and having head notches formed in said collar edge, said collar having a transverse dimension, measured perpendicularly to the screw axis, larger than a transverse dimension of the first thread, also measured perpendicularly to the screw axis.

Such a screw head provided with such a collar allows reinforcing the primary stability of the transpedicular anchoring screw by being implanted in the cortical wall of a pedicle of a vertebra, and also promoting bone regeneration inside the head notches formed in said collar, also improving the secondary stability of said transpedicular anchoring screw.

In one embodiment, at least one amongst a proximal notch and a distal notch is at least partially filled with a bioresorbable material.

According to one possibility, each of the proximal notches and each of the distal notches is at least partially filled with the bioresorbable material.

The first thread then has, before the implantation of the transpedicular anchoring screw according to the disclosure in a vertebra, a substantially non-notched shape, each proximal and distal notch being filled with the bioresorbable material: the transpedicular anchoring screw then has a standard profile substantially similar to that of other known anchoring screws of the prior art.

In this embodiment, the shape and/or the arrangement of the proximal and distal notches therefore has no influence during the implantation of the transpedicular anchoring screw in a vertebra.

In particular, any risk of damage to the bone structure of the pedicle by the distal portion of the first thread is avoided.

Once the transpedicular anchoring screw according to the disclosure has been implanted in a vertebra and after a certain time interval, the bioresorbable material is resorbed so as to enable a bone regeneration of the bone structure of said vertebra in the proximal and distal notches of the first thread thus revealed.

According to one feature, the bioresorbable material is a polymer, for example a PLA (polyactic acid) type polymer, a PLGA (polyglycolic acid) type polymer or a PLA-PLGA type copolymer.

It should be noted that, in a variant of the disclosure, such a bioresorbable material could be used with a bone anchoring screw having at least one thread in which notches are provided, and wherein these notches are at least partially filled with the bioresorbable material.

In other words, such a variant of the disclosure would consist of a bone anchoring screw, for example a transpedicular anchoring screw, suitable for anchorage in a bone, including a screw body extending along a screw axis between a proximal end and a distal end, this screw body having at least one helical-shaped thread with a given thread pitch, extending between the proximal end and the distal end and having a convex-shaped outer edge, wherein this outer edge has a series of notches, and wherein at least one of the notches is at least partially filled with a bioresorbable material.

According to one possibility, each of the notches is at least partially filled with the bioresorbable material.

The aforementioned different features for the disclosure, such as for example the presence of a second thread or the presence of a proximal portion and a distal portion having different notches, could then be applied to this variant.

BRIEF DESCRIPTION OF THE DRAWINGS

Other features and advantages of the present disclosure will appear upon reading the detailed description hereinafter of non-limiting examples of implementation, made with reference to the appended figures in which.

DETAILED DESCRIPTION OF THE DRAWINGS

Figure 1:
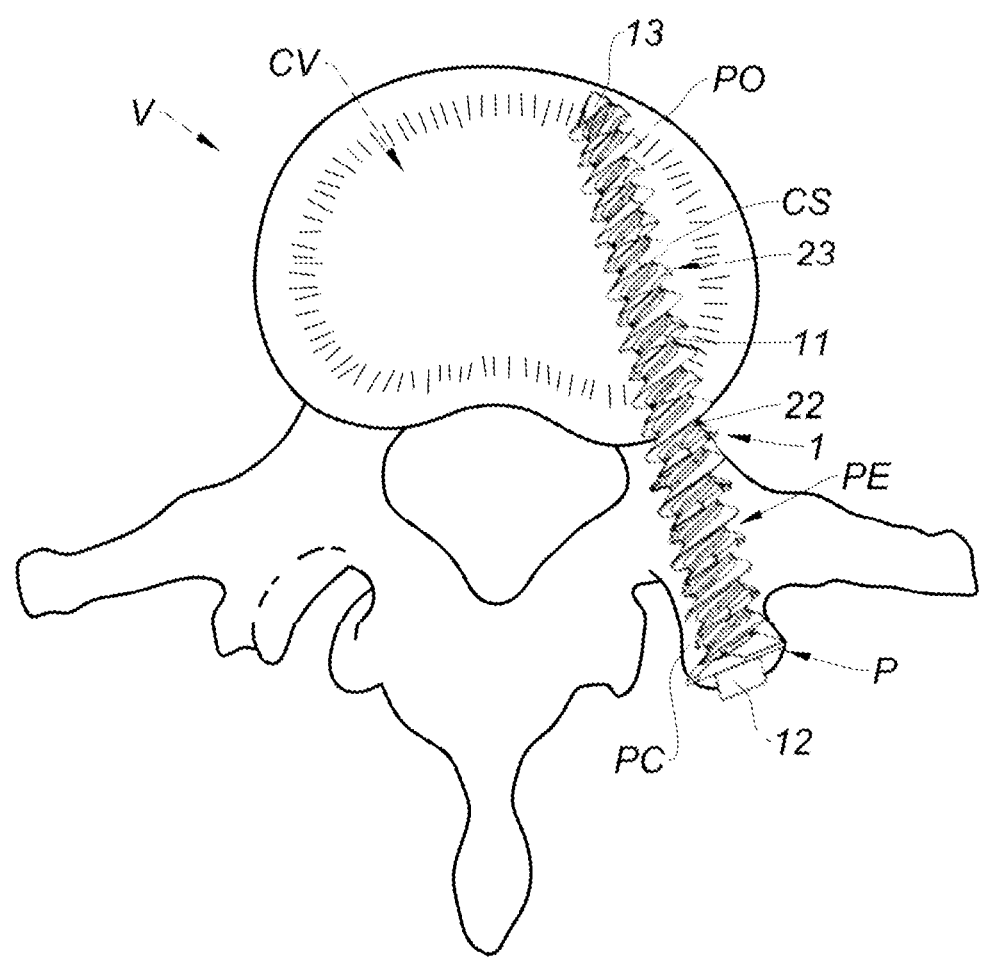
FIG. 1 is a view of a transpedicular anchoring screw according to the disclosure implanted in a vertebra.

FIG. 1 represents a transpedicular anchoring screw 1 according to the disclosure implanted in a vertebra V of a patient through a posterior approach.

The transpedicular anchoring screw 1 has a screw body 11 penetrating a pedicle P and a vertebral body CV of the vertebra V, so that said screw body 11 passes through four types of bone structures of the vertebra V, each having different mechanical properties:
- a cortical wall PC of the pedicle P, formed of a compact and hard bone,
- a central portion PE of the pedicle P, formed of a quite dense spongy bone,
- a spongy body CS of the vertebral body CV, formed of barely dense and fragile bone, and
- the cortical wall PO of the vertebral body CV, formed of a compact and hard bone.

The transpedicular anchoring screw 1 also has a screw head 12 projecting from the pedicle P and adapted to cooperate with a surgical implant (not represented), in order to enable fastening of said surgical implant on the vertebra V.

Finally, the transpedicular anchoring screw 1 has a leading edge 13 anchored in the cortical wall PO of the vertebral body CV.

Figure 2:
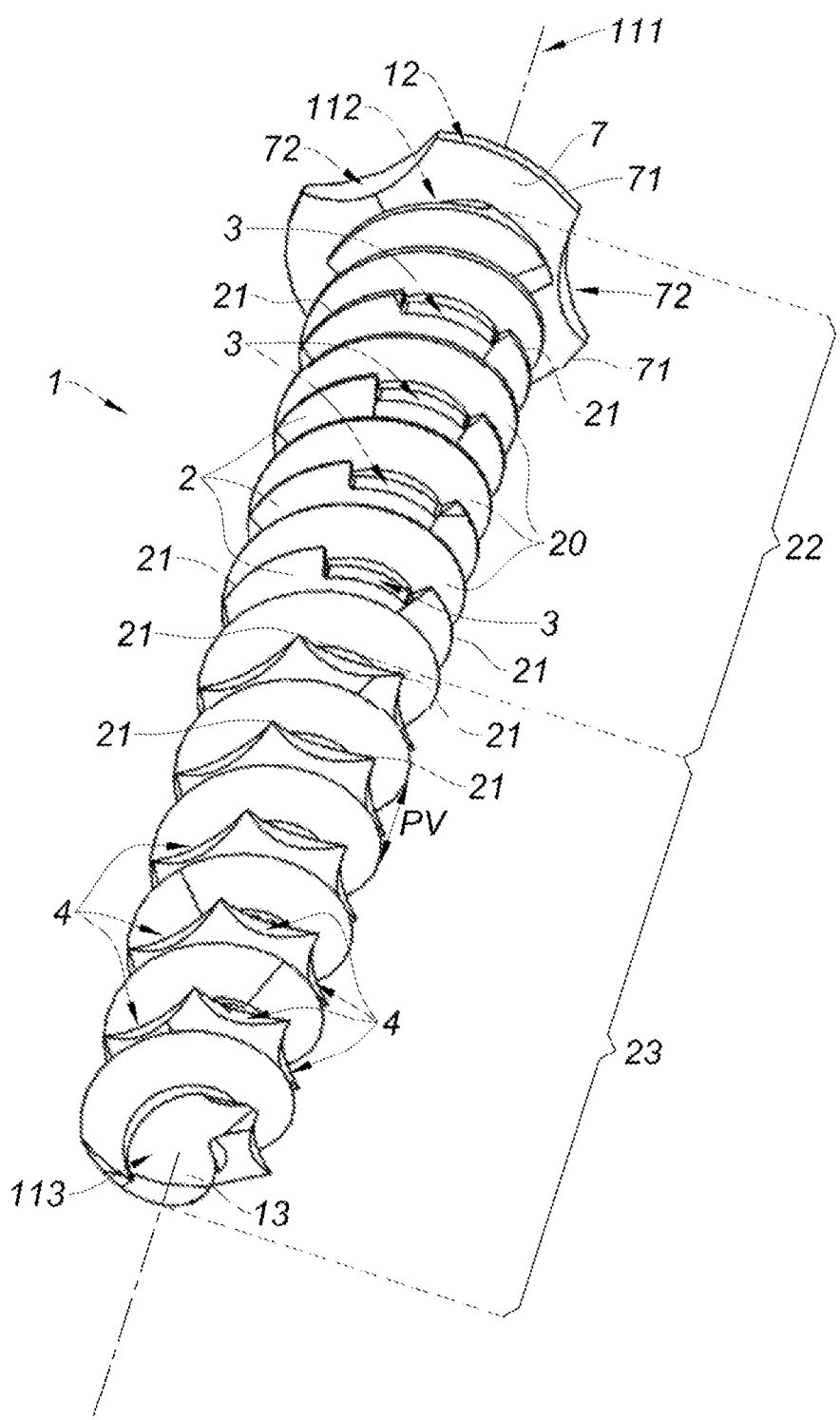
FIG. 2 is a perspective view of a transpedicular anchoring screw according to the disclosure.
Figure 3:
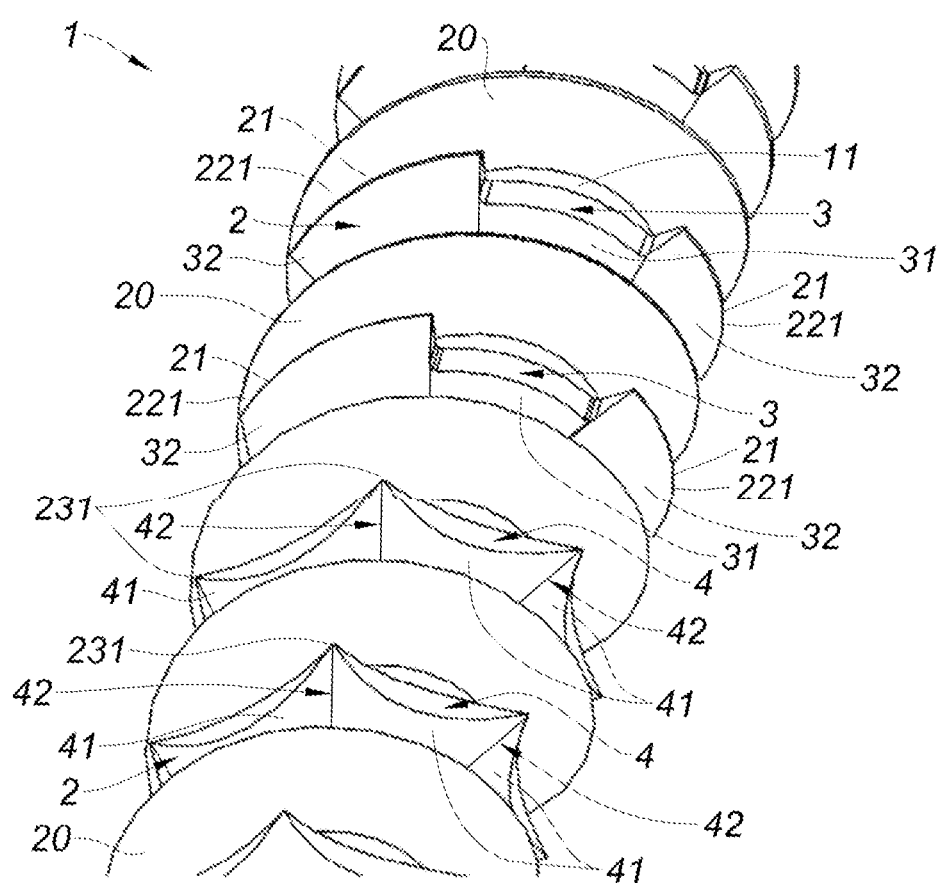
FIG. 3 is a detail view of the transpedicular anchoring screw illustrated by FIG. 2.

Referring to FIGS. 2 and 3, the transpedicular anchoring screw 1 has a geometry adapted to cooperate with the different bone structures of the vertebra V with which it is in contact when the latter is implanted in said vertebra V.

More specifically, the screw body 11 of the transpedicular anchoring screw 1 has a profiled shape, with a circular section, extending along a screw axis 111 between a proximal end 112 and a distal end 113 and is provided with a first thread 2 and a second thread 20, both helical shaped and arranged around the screw body 111 between the screw head 12 and the leading edge 13.

It should be noted that this screw body 11 may be solid. Alternatively, the screw body 11 may be hollow, in other words this screw body 11 may have an inner hole or orifice extending over all or part of its length from its proximal end 112 to its distal end 113. If this inner hole or orifice extends over the entire length and also passes through the screw head 12, it could then be used, for example, for the passage of a wire or a guide.

The first thread 2 and the second thread 20 have the same screw pitch PV and are moreover "nested" with each other, so that the screw body 11 has, along the screw axis 111, an alternation of the first thread 2 and the second thread 20.

The first thread 2 has a particular geometry designed to improve the secondary stability of the transpedicular anchoring screw 1 when the latter is implanted in the vertebra V, as illustrated in the previous FIG. 1.

Indeed, the first thread 2 includes an outer edge 21 disposed, over the entire length of the screw body 11 along the screw axis 111, at a constant distance D from said screw body 11: the screw body 11 having a circular shaped section (in a plane orthogonal to the screw axis 111), the outer edge 21 has a circular spiral shape "winding" around the screw body 11 between the screw head 12 and the leading edge 13.

As shown in FIG. 2, the first thread 2 has, along the screw axis 111, two distinct portions 22, 23 disposed one after another, in which it has a specific shape:
- a proximal portion 22, in contact with the screw head 12, in which proximal notches 3 are formed in the outer edge 21; and a distal portion 23, extending the proximal portion 22 and in contact with the leading edge 13, in which distal notches 4 having a different shape from the proximal notches 3 are formed in the outer edge 21.

Thus, the outer edge 21 (generally convex shaped), has in the proximal portion 22 of the first thread 2 a series of proximal notches 3 (generally concave shaped) separated from each other by non-notched proximal portions 221 of the outer edge 21.

Hence, each proximal notch 3 defines a notched proximal portion 31 of the first thread 2, corresponding to the portion of the first thread 2 comprised between the screw body 11 and said proximal notch 3.

In other words, each notched proximal portion 31 of the first thread 2 corresponds to the portion of said first thread 2 comprised in a notched proximal angular sector 33 (shown in FIGS. 4 and 5) under which each proximal notch 3 is viewed from the screw axis 111.

Similarly, each non-notched proximal portion 221 of the outer edge 21 defines a separation proximal portion 32 of the first thread 2, corresponding to the portion of the first thread 2 comprised between the screw body 11 and said non-notched proximal portion 221.

In other words, each separation proximal portion 32 of the first thread 2 corresponds to the portion of said first thread 2 comprised in a separation proximal angular sector 34 (shown in FIGS. 4 and 5) under which each non-notched proximal portion 221 from screw axis 111.

Thus, the first thread 2 has, from the screw head 12 towards the leading edge 13, an alternation of notched proximal portions 31 and separation proximal portions 32, two successive notched proximal portions 31 being separated from each other by a separation proximal portion 32.

Similarly, the outer edge 21 (generally convex shaped), has in the distal portion 23 of the first thread 2 a series of distal notches 4 (generally concave shaped) separated from each other by non-notched distal portions 231 of the outer edge 21.

Hence, each distal notch 4 defines a notched distal portion 41 of the first thread 2, corresponding to the portion of the first thread 2 comprised between the screw body 11 and said distal notch 4.

In other words, each notched distal portion 41 of the first thread 2 corresponds to the portion of said first thread 2 comprised in a notched distal angular sector 43 (shown in FIGS. 4 and 5) under which each distal notch 4 is viewed from the screw axis 111.

Similarly, each non-notched distal portion 231 of the outer edge 21 defines a separation distal portion 42 of the first thread 2, corresponding to the portion of the first thread 2 comprised between the screw body 11 and said non-notched distal portion 231.

In other words, each separation distal portion 42 of the first thread 2 corresponds to the portion of said first thread 2 comprised in a separation distal angular sector 44 (shown in FIGS. 4 and 5) under which each non-notched distal portion 231 is viewed from screw axis 111.

Thus, the first thread 2 has, in its distal portion 23, an alternation of notched distal portions 41 and separation distal portions 42, two successive notched distal portions 41 being separated from each other by a separation distal portion 42.

The presence of the proximal notches 3 and the distal notches 4 allows improving the secondary stability of the transpedicular anchoring screw 1 according to the disclosure.

Indeed, once implanted in the vertebra V, these proximal notches 3 and these distal notches 4 promote bone regeneration of said vertebra V: some time after the operation of implanting in the vertebra V, these proximal notches 3 and these distal notches 4 are at least partially filled with new bone structures.

Due to their extended contact with the first thread 2, these new bone structures increase the intensity of the mechanical forces exerted between the vertebra V and the transpedicular anchoring screw 1, thus improving the secondary stability of the transpedicular anchoring screw 1.

Conversely, the separation proximal portions 32 and the separation distal portions 42 present, upon implantation of the transpedicular anchoring screw 1 in the vertebra V, a large contact surface therewith and therefore contribute to the primary stability of this transpedicular anchoring screw 1.

Thus, the larger the surface occupied by the proximal 3 and distal 4 notches, the more the transpedicular anchoring screw will have a significant secondary stability, but the increase in the size of these proximal 3 and distal 4 notches results in a reduction of the surface occupied by the separation proximal portions 32 and the separation distal portions 42: the improvement of the secondary stability of the transpedicular anchoring screw 1 by means of the proximal 3 and distal 4 notches is therefore done to the detriment of its primary stability.

Hence, the particular geometry of the first thread 2 in its proximal portion 22 and in its distal portion 23 addresses the search for an optimization of the size of the surface occupied by the proximal 3 and distal 4 notches with respect to that of the surface occupied by the separation proximal portions 32 and the separation distal portions 42, in order to improve the secondary stability of the transpedicular anchoring screw 1 without deteriorating its primary stability.

As shown in FIG. 1, the distal portion 23 of the first thread 2 is implanted in the spongy body CS of the vertebral body CV: this bone structure being formed of a fragile and low-density bone, the primary stability resulting from the contact between the spongy body CS and the separation distal portions 42 is therefore very small in comparison with the size of the separation distal portions 42.

Figure 6:
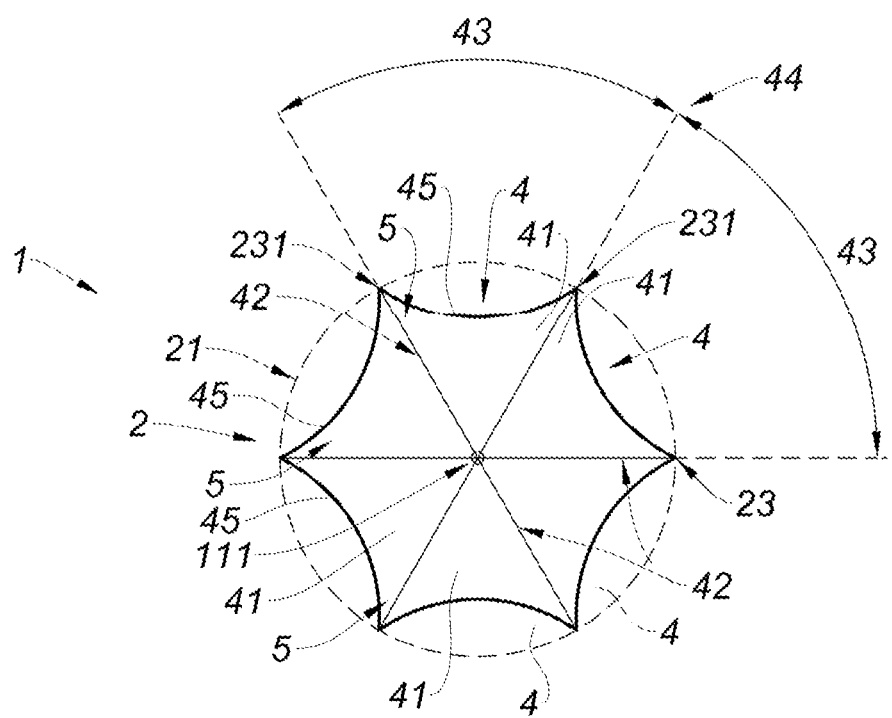
FIG. 6 is a schematic representation of the first thread in its distal portion.

Thus, it is possible to significantly reduce the surface of these separation distal portions 42 without the overall primary stability of the transpedicular anchoring screw 1 being considerably degraded: it is therefore advantageous to increase the size of the distal notches 4 in comparison with that of the separation distal portions 42, in order to significantly increase the secondary stability conferred by the distal portion 23 of the first thread 2. As shown in FIG. 6, representing the first thread 2 viewed from the screw axis 111 over a length of one screw thread PV, the successive distal notches 4 are actually contiguous: each non-notched distal portion 231 of the outer edge 21 is thus reduced, in the distal portion 23, to a single point of contact between two successive distal notches 4.

Thus, each separation distal portion 42 is also reduced to a line segment joining this point of contact and the screw body 11: the surface occupied by the separation distal portions 42 is therefore zero.

Similarly, the measurement of the separation distal angular sectors 44, in which the separation distal portions 42 are inscribed, is zero.

Conversely, the distal notches 4 are present in a large number and have a large size: the notched distal angular sectors 43, under which the distal notches 4 are viewed and in which the notched distal portions 41 are inscribed, have a measurement equal to 60°.

Over a length of the first thread 2 corresponding to one screw pitch PV, the first thread 2 thus has six contiguous distal notches (and also six notched distal portions 41). It should be noted that, in the embodiment represented in FIG. 6, all distal notches 4 have the same shape and the same size, and the notched distal angular sectors 43 have the same extent: other embodiments could of course be considered.

Thus, in the distal portion 23, over this length of the first thread 2 corresponding to one screw pitch PV, a ratio between the sum of the measurements of all of the separation distal angular sectors 44 and the sum of the measurements of all of the notched distal angular sectors 43 is equal to 0 (and is therefore in particular comprised between 0% and 10%): in the distal portion 23 of the first thread 2, the notched distal portions 41 therefore occupy a large surface in comparison with the separation distal portions 42, allowing greatly increasing the secondary stability conferred by this distal portion 23.

Conversely, as shown in FIG. 1, the proximal portion 22 of the first thread 2 is implanted in the pedicle P of the vertebra V and is therefore in contact with the cortical wall PC and the central portion PE: these bone structures being formed of a dense and solid bone, the primary stability resulting from the contact between the pedicle P and the separation proximal portions 32 is therefore very significant and proportional to the size of the surface occupied by these.

It is then impossible to significantly reduce the surface of these separation proximal portions 32 without the overall primary stability of the transpedicular anchoring screw 1 being greatly degraded: it is therefore necessary to limit the size of the proximal notches 3 and to keep a large size of the separation proximal portions 32, in order to slightly increase the secondary stability conferred by the proximal portion 22 of the first thread 2 while preserving a good primary stability.

Figure 4:
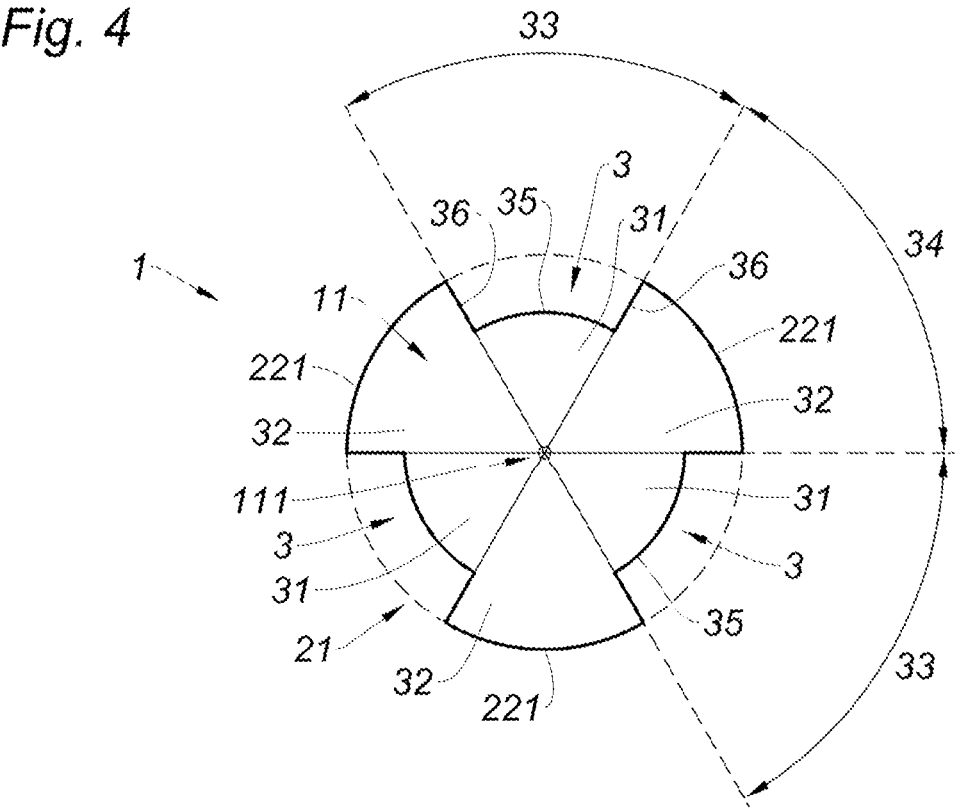
FIG. 4 is a schematic representation of the first thread in its proximal portion according to a first embodiment.
Figure 5:
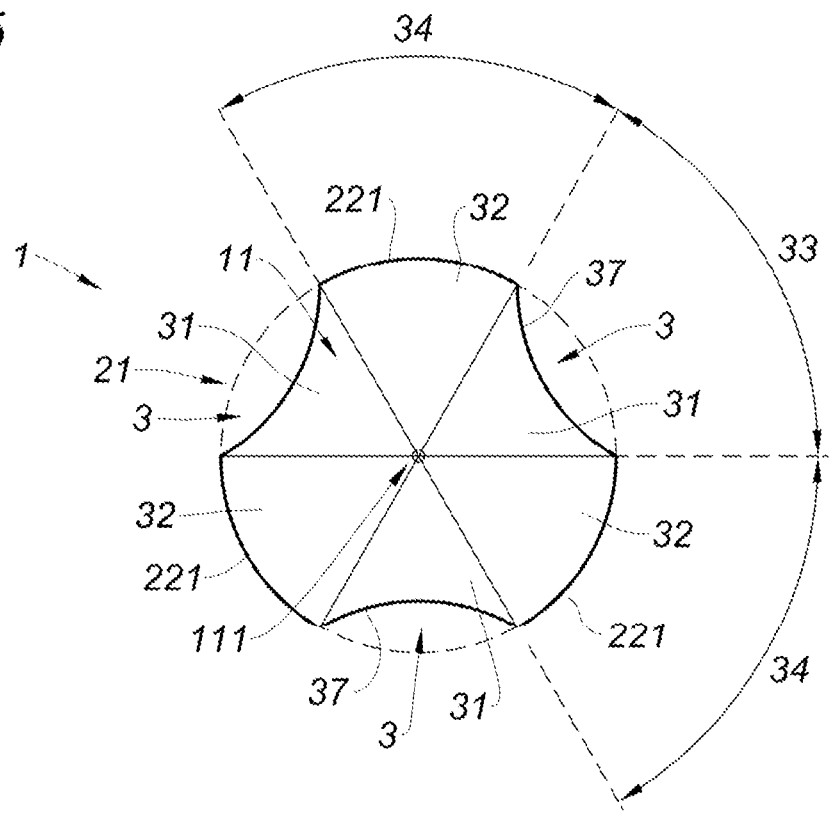
FIG. 5 is a schematic representation of the first thread in its proximal portion according to a second embodiment.

As shown in FIGS. 4 and 5, respectively representing the first thread 2 viewed from the screw axis 111 over a length of a screw pitch PV according to a first embodiment and according to a second embodiment, the successive proximal notches 3 are not contiguous and are separated by non-notched portions 221 of the outer edge 21 with a non-zero length: the successive notched proximal portions 31 are thus separated by a large-sized separation proximal portion 32.

In the two embodiments represented in FIGS. 4 and 5, the separation proximal angular sectors 34, in which the separation proximal portions 32 are inscribed, and the notched proximal angular sectors 33, in which the notched proximal portions 31 are inscribed, have the same extent, equal to 60°.

Thus, in the proximal portion 22, over this length of the first thread 2 corresponding to one screw pitch PV, a ratio between the sum of the measurements of all of the separation proximal angular sectors 34 and the sum of the measurements of all of the notched proximal angular sectors 33 is equal to 1 (and is therefore in particular comprised between 0% and 150%).

Over a length of the first thread 2 corresponding to one screw pitch PV, the first thread 2 thus has only three proximal notches 3 (and therefore three notched proximal portions 31).

It should be noted that, in the embodiment represented in FIGS. 4 and 5, all proximal notches 3 have the same shape and the same size, and the notched proximal angular sectors 33 have the same extent: other embodiments could of course be considered.

Similarly, all separation proximal portions 32 have the same shape and the same size, and the separation proximal angular sectors 34 have the same extent: other embodiments could also be considered.

The balance between the surface occupied by the separation proximal portions 32 and that one occupied by the notched proximal portions 31 thus allows improving the secondary stability conferred by the proximal portion 22 of the transpedicular anchoring screw 1, while preserving a good primary stability.

It should be noted that in FIGS. 4, 5 and 6, the outer edge 21 is represented, in the notched proximal portions 31 and the notched distal portions 41, by a dotted line (coinciding with the non-notched portions 221 and the non-notched portions 231 respectively in the separation proximal portions 31 and the separation distal portions 41): it is with respect to this outer edge 21 that the proximal 3 and distal 4 notches are defined.

Many embodiments could be considered regarding the particular shape of these proximal 3 and distal 4 notches.

For example, in the first embodiment represented by FIG. 4, each proximal notch 3 is delimited by:
- a notch edge 35 shaped as a convex circle arc, and
- two lateral flanges 36 extending radially with respect to the screw axis 111 and joining the notch edge 35 and the non-notched portions 221 adjacent to the proximal notch 3.

In the second embodiment represented by FIG. 5, each proximal notch 3 is delimited by a single notch edge 37 shaped as a concave circle arc, joining the non-notched portions 221 adjacent to the proximal notch 3.

Similarly, as shown in FIG. 6, each distal notch 4 is delimited by a single notch edge 45 shaped as a concave circle arc, joining the non-notched portions 231 adjacent to the proximal notch 4.

It should be noted that, because the distal notches 4 are contiguous, the first thread 2 has in the distal portion 23 a "star"-like shape, two successive distal notches 4 forming therebetween a radial projection 5 in the form of a point.

As mentioned before, these radial projections 5 allow creating at their periphery a bone remodeling area which also promotes the secondary stability of the transpedicular anchoring screw 1.

Figure 7:
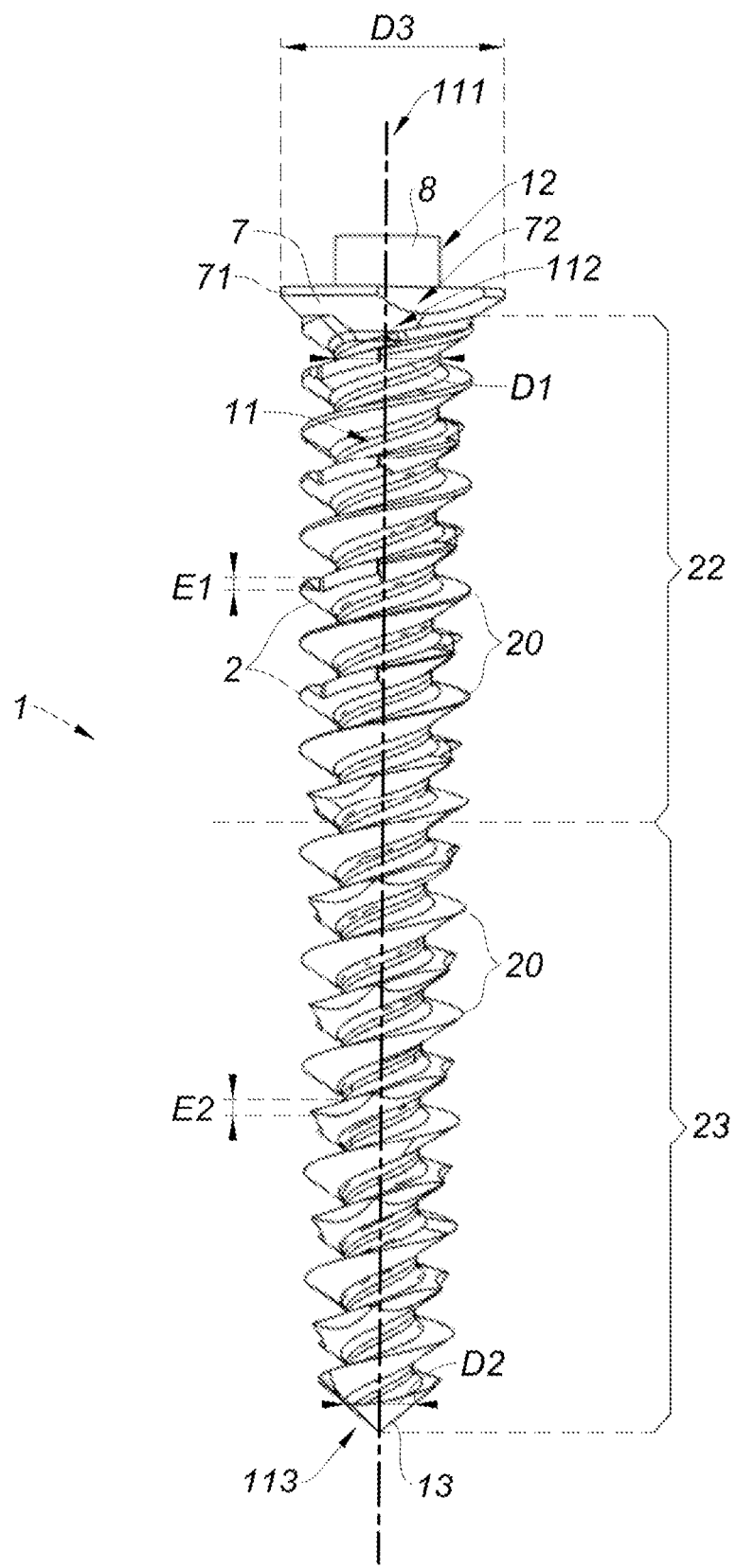
FIG. 7 is a profile view of a transpedicular anchoring screw according to the disclosure.

Moreover, as shown in FIG. 7, the first thread 2 has in its proximal portion 22 a thickness E1, measured along the screw axis 111, larger than a thickness E2 of the same first thread 2 in its distal portion 23.

In addition, the screw body 11 has a slightly conical shape and has a transverse dimension (corresponding to the diameter of its circular section), measured perpendicularly to the screw axis 111, whose measurement progressively decreases between the proximal end 112 and the distal end 113.

Thus, the screw body 11 has a maximum transverse dimension D1 at the proximal end 112 and a minimum transverse dimension D2 at the distal end 113.

This reduction in the transverse dimension of the screw body and the thickness of the first thread 2 between the proximal portion 22 and the distal portion 23 allows preventing the distal portion 23 from damaging the bone structure of the pedicle P (in which the proximal portion 22 will be ultimately implanted) during the introduction of the transpedicular anchoring screw 1 into the vertebra V.

In this way, the primary stability of the transpedicular anchoring screw 1 conferred by the proximal portion 22 is not deteriorated by the prior passage of the distal portion 23 in the pedicle P.

The screw head 12 also has a structure adapted to promote the primary and secondary stability of the transpedicular anchoring screw 1.

Indeed, this screw head has in particular a collar 7 delimited by a collar edge 71, in which head notches 72 are formed.

This collar 7 has a transverse dimension D3 with a measurement larger than the maximum transverse dimension D1 of the first thread 2: this collar 7, once implanted in the cortical wall PC of the pedicle P, thus has a large contact surface with the bone structure of this pedicle P and significantly contributes to the primary stability of the transpedicular anchoring screw 1.

In the same manner as the proximal 3 or distal 4 notches of the first thread 2, the head notches 72 promote bone regeneration of the pedicle P after the implantation of the transpedicular anchoring screw 1 in the latter, thus contributing to the secondary stability of this transpedicular anchoring screw 1.

It should be noted that the geometry of the head 12 may also be illustrated by FIG. 5, the represented proximal notches 3 (formed in the outer edge 21) then corresponding to the head notches 72 formed in the edge of the collar 71.

Of course, many other embodiments concerning the geometry of this flange 7 are possible.

It should be noted that the screw head 12 also has an end piece 8, intended to project from the pedicle P once the transpedicular anchoring screw 1 has been implanted in the vertebra V, said endpiece 8 being adapted to cooperate with a surgical implant intended to be fastened on said vertebra V by means of the transpedicular anchoring screw 1.

The primary stability of the transpedicular anchoring screw 1 is also ensured by the presence of the second thread 20.

Indeed, as shown in FIGS. 2, 3 and 7, this second thread 20 has a shape similar to that of the first thread 2, but is devoid of proximal or distal notches.

Hence, this second thread 20 has a very large contact surface with the bone structures of the vertebra V in which the transpedicular anchoring screw 1 is implanted, thereby guaranteeing a very good primary stability to this transpedicular anchoring screw 1.

Yet, this second thread 20 contributes only marginally to the secondary stability of the transpedicular anchoring screw 1.

Figure 8:
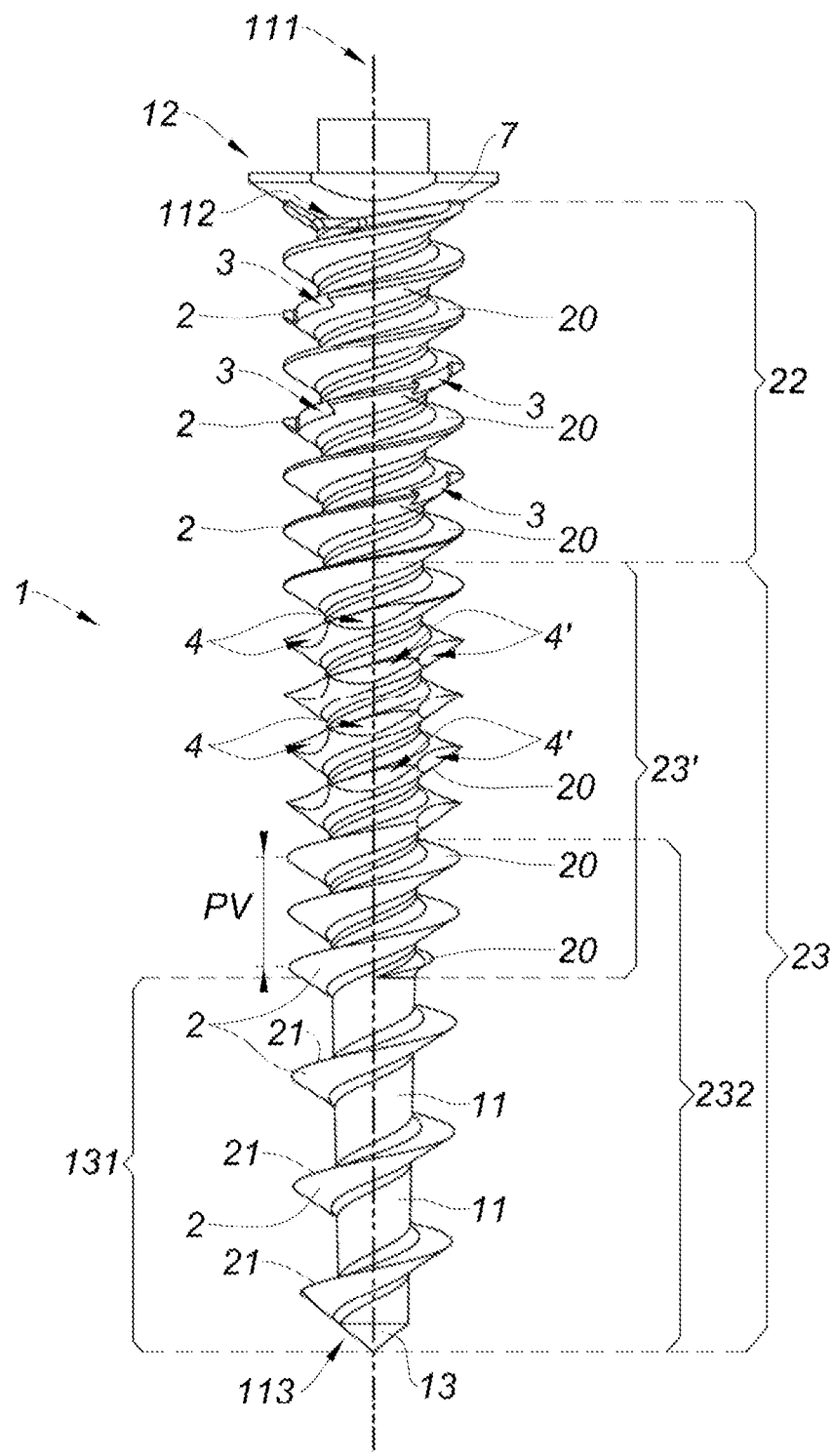
FIG. 8 is a profile view of a transpedicular anchoring screw according to an alternative embodiment of the disclosure.

FIG. 8 represents an alternative embodiment of the disclosure, identical to the embodiment previously described by FIGS. 1 to 6 with the exception of the geometry and the structure of the first thread 2 and of the second thread 20.

In particular, the first thread 2 herein has, in its distal portion 23, a distal sub-portion 232 close to the leading edge 13 in which the outer edge 21 includes no distal notch 4.

However, the first thread 2 has distal notches 4, identical to those described before and shown in particular in FIG. 2, 3 or 6 and having the same function, in the rest of its distal portion 23, proximate to its proximal portion 22.

Moreover, in this alternative embodiment, the second thread 20 does not extend up the leading edge 13 and thus has a distal portion 23' shorter than the distal portion 23 of the first thread 2.

Thus, the transpedicular anchoring screw 1 of FIG. 8 has a tip portion 131 having only a single thread devoid of notches, namely a portion of the distal sub-portion 232 of the first thread 2: this feature allows promoting and facilitating the penetration of said transpedicular anchoring screw 1 into the bone structure of a vertebra V.

In addition, due to the absence of distal notches 4 in this tip portion 131, the transpedicular anchoring screw 1 has no radial projection in the form of a point proximate to the leading edge 13, which allows limiting the risk of deterioration of the bone structures that said transpedicular anchoring screw 1 is brought to pass through during the implantation thereof in a vertebra V.

Finally, the second thread 20 has, in its distal portion 23', distal notches 4' having the same shape and the same function as the distal notches 4 formed in the first thread 2 and described before.

In particular, the geometry and the distribution of these distal notches 4' may be illustrated by those of the distal notches 4 represented in FIG. 6.

Hence, this second thread 20 also has, in its distal portion 23', a "star"-like shape allowing maximizing the secondary stability conferred for the transpedicular anchoring screw 1.

Thus, the overall secondary stability of the transpedicular anchoring screw 1 of FIG. 8 is equivalent to that of the previous embodiment because, although this transpedicular anchoring screw 1 does not include any distal notch proximate to the leading edge 13, it includes a much larger number proximate to the proximal portion 22.

Moreover, and as in the previous embodiment, the second thread 20 has no proximal notch in its distal portion 22 (whereas the first thread 2 has proximal notches 3 identical to those described before and shown in particular in FIGS. 2 to 5): therefore, the proximal portion 22 of the second thread 20 contributes only very slightly to the secondary stability of the transpedicular anchoring screw 1, but allows guaranteeing a high primary stability thanks to the large contact surfaces that it has with the surrounding bone structures once this transpedicular anchoring screw 1 is implanted in a vertebra V.

Thus, this alternative embodiment allows facilitating the insertion of the transpedicular anchoring screw 1 into a vertebra V while avoiding deteriorating the latter, while having primary stability and secondary stability substantially equivalent to the previous embodiment.

As described before, it could also be considered that, in either one of the previously-described embodiments, the proximal notches 3 and the distal notches 4 or 4' are at least partially filled, before implantation of the transpedicular anchoring screw 1 in the vertebra V, by a bioresorbable material, for example a PLA (polyactic acid) type polymer, a PLGA (polyglycolic acid) type polymer or a PLA-PLGA type copolymer. Preferably, the proximal notches 3 and the distal notches 4 or 4' are fully filled so that the bioresorbable material confers continuity with the outer edge 21 of the first thread 2, and possibly with the outer edge of the second thread 20 in the case wherein the latter is also provided with notches.

In this manner, during the introduction of the transpedicular anchoring screw 1 into the vertebra V, any risk of damage to the bone structure of the latter due to the presence of the proximal notches 3 or the distal notches 4 or 4' is avoided.

After the operation of implanting the transpedicular anchoring screw 1 in the vertebra V, the bioresorbable material is resorbed and the proximal 3 and distal 4 or 4' notches are uncovered and could become the site of a bone regeneration contributing, as described hereinabove, to the secondary stability of the transpedicular anchoring screw 1.

Thus, the transpedicular anchoring screw 1 according to the disclosure has a geometry adapted to the different bone structures of the vertebra V in which it is intended to be implanted, said geometry allowing significantly improving the secondary stability of this transpedicular anchoring screw 1 in comparison with the anchoring screws of the prior art, without degrading its primary stability.

The invention claimed is:

1. A transpedicular anchoring screw, adapted for anchorage in a pedicle of a vertebra, including a screw body extending along a screw axis between a proximal end and a distal end, said screw body having a first thread and a second thread, each of said first thread and second thread being helical-shaped with a same screw pitch, extending between said proximal end and said distal end and having a convex-shaped outer edge, said transpedicular anchoring screw being characterized in that at least said first thread has, from the proximal end towards the distal end, at least:

a proximal portion, in which the outer edge of said first thread has a series of notched proximal portions, each defined by a proximal notch formed in said outer edge and inscribed within a notched proximal angular sector, wherein two successive notched proximal portions are separated from each other by a separation proximal portion, in which said outer edge is not notched and is inscribed within a separation proximal angular sector, and wherein, over a length of the first thread corresponding to one screw pitch (PV), a ratio between the sum of the measurements of all of the separation proximal angular sectors and the sum of the measurements of all of the notched proximal angular sectors is comprised between 50% and 150%; and a distal portion, in which the outer edge of said first thread has a series of notched distal portions, each defined by a distal notch formed in said outer edge and inscribed within a notched distal angular sector, wherein two successive notched distal portions are separated by a separation distal portion, in which said outer edge is not notched and is inscribed within a separation distal angular sector, and wherein, over a length of the first thread corresponding to one screw pitch, a ratio between the sum of the measurements of all of the separation distal angular sectors and the sum of the measurements of all of the notched distal angular sectors is comprised between 0% and 10%.

2. The transpedicular anchoring screw according to claim 1, wherein each proximal notch has an identical shape and wherein each separation proximal portion is inscribed within a respective separation proximal angular sector with an identical extent, so that said proximal notches are evenly spaced from each other along said first thread.

3. The transpedicular anchoring screw according to claim 2, wherein each notched proximal portion and each separation proximal portion is inscribed within a respective notched proximal angular sector or separation proximal angular sector with an identical measurement within 5°.

4. The transpedicular anchoring screw according to claim 3, wherein the measurement of each of said notched proximal angular sectors or separation proximal angular sectors is comprised between 30° and 75°.

5. The transpedicular anchoring screw according to claims 1, wherein at least one of the proximal notches is delimited by a single notch edge shaped as a concave circle arc.

6. The transpedicular anchoring screw according to claim 1, wherein at least one of the proximal notches is delimited by a notch edge shaped as a convex circle arc.

7. The transpedicular anchoring screw according to claim 1, wherein the proximal portion and the distal portion are contiguous, one of the separation proximal portions of the proximal portion being contiguous to one of the notched distal portions of the distal portion.

8. The transpedicular anchoring screw according to claim 1, wherein each of the separation distal portions is inscribed within a separation distal angular sector whose measurement is equal to 0°, so that the successive distal notches are contiguous.

9. The transpedicular anchoring screw according to claim 1, wherein at least one of the distal notches is delimited by a single notch edge shaped as a concave circle arc.

10. The transpedicular anchoring screw according to claim 1, wherein each notched distal portion is inscribed within a notched distal angular sector whose measurement is comprised between 50° and 75°.

11. The transpedicular anchoring screw according to claim 1, wherein the notched proximal portions and the separation proximal portions of the proximal portion have a thickness (E1), measured along the screw axis (111), larger than a thickness of the notched distal portions and of the separation distal portions of the distal portion.

12. The transpedicular anchoring screw according to claim 1, wherein the proximal portion and the distal portion of the first thread extend respectively, along the screw axis, over a proximal length and a distal length, said proximal length having an measurement comprised between 0.5 and 1.5 times that of said distal length.

13. The transpedicular anchoring screw according to claim 1, wherein the screw body has a transverse dimension, measured perpendicularly to the screw axis, whose measurement progressively decreases between the proximal end and the distal end.

14. The transpedicular anchoring screw according to claim 1, including a screw head positioned on the proximal end of the screw body, said screw head having a collar delimited by a convex-shaped collar edge and having head notches formed in said collar edge, said collar having a transverse dimension, measured perpendicularly to the screw axis, larger than a transverse dimension of the first thread, also measured perpendicularly to the screw axis.

15. The transpedicular anchoring screw according to claim 1, wherein at least one amongst a proximal notch and a distal notch is at least partially filled with a bioresorbable material.

16. The transpedicular anchoring screw according to claim 15, wherein each of the proximal notches and each of the distal notches is at least partially filled with the bioresorbable material.

17. The transpedicular anchoring screw according to claim 15, wherein the bioresorbable material is a polymer, for example a PLA (polyactic acid) type polymer, a PLGA (polyglycolic acid) type polymer or a PLA-PLGA type copolymer.

* * * * *